(12) United States Patent
Barnhart et al.

(10) Patent No.: US 10,704,993 B2
(45) Date of Patent: Jul. 7, 2020

(54) SUBSURFACE ENVIRONMENT SAMPLER WITH ACTUATOR MOVABLE COLLECTION CHAMBER

(71) Applicants: Elliott Barnhart, Clancy, MT (US); Robert Hyatt, Butte, MT (US); Mathew Fields, Bozeman, MT (US); Alfred B Cunningham, Bozeman, MT (US)

(72) Inventors: Elliott Barnhart, Clancy, MT (US); Robert Hyatt, Butte, MT (US); Mathew Fields, Bozeman, MT (US); Alfred B Cunningham, Bozeman, MT (US)

(73) Assignee: United States of America as represented by the Secretary of the Department of the Interior, Washington, DC (US)

( * ) Notice: Subject to any disclaimer, the term of this patent is extended or adjusted under 35 U.S.C. 154(b) by 149 days.

(21) Appl. No.: 15/615,794

(22) Filed: Jun. 6, 2017

(65) Prior Publication Data
US 2018/0348093 A1 Dec. 6, 2018

(51) Int. Cl.
*G01N 1/18* (2006.01)
*G01N 1/12* (2006.01)
(Continued)

(52) U.S. Cl.
CPC .............. *G01N 1/18* (2013.01); *C12Q 1/025* (2013.01); *C12Q 1/64* (2013.01); *E21B 49/082* (2013.01);
(Continued)

(58) Field of Classification Search
CPC ... G01N 1/18; G01N 1/12; C12Q 1/64; E21B 49/08
(Continued)

(56) References Cited

U.S. PATENT DOCUMENTS

| 166,136 | A | * | 7/1875 | Patterson | ................... E21B 7/26 |
| | | | | | 175/22 |
| 767,209 | A | * | 8/1904 | Decker | ..................... E21B 7/26 |
| | | | | | 166/230 |

(Continued)

OTHER PUBLICATIONS

Harrison, W. D. et al, Water Resources Research 1981, 17, 1731-1736.*
(Continued)

*Primary Examiner* — Arlen Soderquist
(74) *Attorney, Agent, or Firm* — James Mitchell (57) ABSTRACT

A Sampler and process for collecting, growing, inoculating and evaluating microbes in-situ. The Sampler may be loaded with an active or inert media to assist with the collection of microbes. It is closed and lowered to a desired depth. Sampler is opened to initiate sampling. Materials are added to the sampler to stimulate growth or change the environment. To collect and grow in situ microbes, the sampler is left open for a period of time, a trigger closes and seals the sampler capturing contents specific to that location. The sampler is lifted preserving the in-situ conditions from the collection location. The contents of the sampler can be interrogated through sealed ports at the field site or at a remote location. The sampler can also be utilized as a biologic reactor allowing researchers to connect laboratory equipment to analyze, modify, or cultivate the collected sample.

20 Claims, 6 Drawing Sheets

(51) Int. Cl.
*C12Q 1/64* (2006.01)
*E21B 49/08* (2006.01)
*G01N 1/22* (2006.01)
*C12Q 1/02* (2006.01)
*G01N 1/10* (2006.01)

(52) U.S. Cl.
CPC ............. *G01N 1/12* (2013.01); *G01N 1/2294* (2013.01); *G01N 2001/1031* (2013.01)

(58) Field of Classification Search
USPC ........................................................ 436/28
See application file for complete search history.

(56) References Cited

U.S. PATENT DOCUMENTS

| | | | | |
|---|---|---|---|---|
| 1,211,415 A * | 1/1917 | Cross | E21B 7/26 | 166/105 |
| 2,374,227 A * | 4/1945 | Metcalf | G01V 9/007 | 166/165 |
| 2,376,366 A * | 5/1945 | Lawlor | G01V 9/007 | 166/165 |
| 3,556,211 A * | 1/1971 | Floyd | E21B 49/082 | 166/163 |
| 3,934,468 A * | 1/1976 | Brieger | E21B 49/10 | 73/152.25 |
| 4,050,315 A * | 9/1977 | Markfelt | E21B 49/082 | 73/864.66 |
| 4,210,025 A * | 7/1980 | Bimond | E21B 49/081 | 73/864.62 |
| 4,235,244 A * | 11/1980 | Abele | A61B 10/04 | 600/562 |
| 4,438,654 A * | 3/1984 | Torstensson | E02D 1/06 | 166/264 |
| 4,538,683 A * | 9/1985 | Chulick | E21B 49/084 | 166/191 |
| 4,669,554 A * | 6/1987 | Cordry | E21B 49/081 | 166/169 |
| 4,721,157 A * | 1/1988 | Berzin | E21B 49/081 | 166/169 |
| 4,804,050 A * | 2/1989 | Kerfoot | E21B 7/26 | 175/20 |
| 4,807,707 A * | 2/1989 | Handley | E21B 7/26 | 175/20 |
| 4,838,079 A * | 6/1989 | Harris | E21B 17/18 | 166/127 |
| 5,046,568 A * | 9/1991 | Cordry | E21B 7/26 | 166/264 |
| 5,058,674 A * | 10/1991 | Schultz | E21B 49/082 | 166/164 |
| 5,146,998 A * | 9/1992 | Cordry | E21B 7/26 | 166/264 |
| 5,168,765 A | 12/1992 | Broussard | | |
| 5,327,981 A * | 7/1994 | Morgan | E02D 1/06 | 166/162 |
| 5,337,822 A * | 8/1994 | Massie | E21B 49/082 | 166/264 |
| 5,337,838 A * | 8/1994 | Sorensen | E21B 49/08 | 166/264 |
| 5,440,941 A * | 8/1995 | Kalidindi | G01N 1/08 | 73/864.64 |
| 5,487,314 A | 1/1996 | Phillips | | |
| 5,487,431 A * | 1/1996 | Webb | E21B 7/205 | 175/20 |
| 5,587,538 A * | 12/1996 | Bratton | G01N 1/14 | 73/863.33 |
| 5,662,166 A * | 9/1997 | Shammai | E21B 49/082 | 166/169 |
| 5,889,217 A * | 3/1999 | Rossabi | E02D 1/025 | 73/864.74 |
| 6,085,576 A * | 7/2000 | Sunshine | G01N 33/0031 | 340/634 |
| 6,189,392 B1 * | 2/2001 | Schultz | E21B 49/081 | 73/864 |
| 6,196,333 B1 * | 3/2001 | Aardal | E21B 7/124 | 175/5 |
| 6,230,820 B1 * | 5/2001 | Cordry | E21B 7/26 | 175/20 |
| 6,487,920 B1 * | 12/2002 | Robbat, Jr. | E21B 7/26 | 73/863.12 |
| 7,234,362 B2 * | 6/2007 | Shinn, II | G01N 33/24 | 73/784 |
| 7,294,259 B2 | 11/2007 | Cote | | |
| 7,392,719 B2 * | 7/2008 | Lee | G01N 1/16 | 166/165 |
| 8,429,986 B2 * | 4/2013 | Lee | G01N 1/16 | 73/863.31 |
| 8,444,937 B2 * | 5/2013 | Tuli | G01V 9/00 | 175/59 |
| 8,646,533 B2 * | 2/2014 | Nguy | E21B 34/14 | 166/332.1 |
| 8,991,483 B2 * | 3/2015 | Irani | E21B 49/082 | 166/66.4 |
| 9,116,087 B2 | 8/2015 | Haywood | | |
| 2004/0050185 A1 * | 3/2004 | Tibbets | G01N 1/08 | 73/864.64 |
| 2004/0089079 A1 * | 5/2004 | Engebretson | E21B 49/08 | 73/863.23 |
| 2004/0129070 A1 * | 7/2004 | Bolze | E21B 49/081 | 73/152.02 |
| 2006/0107770 A1 * | 5/2006 | Lee | G01N 1/16 | 73/864.41 |
| 2008/0076147 A1 | 3/2008 | El-Azizi | | |
| 2009/0241658 A1 * | 10/2009 | Irani | E21B 49/081 | 73/152.23 |
| 2011/0242530 A1 * | 10/2011 | Tuli | G01V 9/00 | 356/300 |
| 2011/0259595 A1 * | 10/2011 | Nguy | E21B 34/14 | 166/332.1 |
| 2011/0315372 A1 * | 12/2011 | Church | E21B 17/1078 | 166/147 |
| 2012/0031205 A1 * | 2/2012 | Lee | G01N 1/12 | 73/864 |
| 2013/0029324 A1 * | 1/2013 | Rajagopal | B01L 3/502 | 435/6.1 |
| 2013/0167666 A1 * | 7/2013 | Jenkins | G01N 1/02 | 73/863.23 |
| 2013/0213645 A1 * | 8/2013 | Proett | E21B 49/10 | 166/250.17 |
| 2013/0248181 A1 * | 9/2013 | Getzlaf | E21B 21/103 | 166/285 |
| 2014/0027105 A1 * | 1/2014 | Irani | E21B 49/082 | 166/66.4 |
| 2015/0075302 A1 * | 3/2015 | Jenkins | G01N 1/2035 | 73/863.23 |

OTHER PUBLICATIONS

Martin, J. B. et al, Limnology and Oceanography: Methods 2004, 2, 398-405.*
Barnhart, E. P. et al, International Journal of Coal Geology 2013, 115, 64-70.*
Elliott Barnhart, Subsurface Environment Sampler for Improved In Situ Characterization of Subsurface Microbial Communities, AGU Fall Meeting Abstracts (Dec. 2016).

* cited by examiner

SUBSURFACE ENVIRONMENT SAMPLER WITH ACTUATOR MOVABLE COLLECTION CHAMBER

STATEMENT REGARDING FEDERALLY SPONSORED RESEARCH OR DEVELOPMENT

The invention described herein was made by employees of the United States Government and may be manufactured and used by the Government of the United States of America for governmental purposes without payment of royalties.

CROSS-REFERENCE TO RELATED APPLICATIONS

This application claims the benefit of U.S. Provisional Application No. 62/333,616, filed May 9, 2016.

FIELD OF THE INVENTION

The present invention is related to a product and process for evaluating subsurface environments such as microbials, water and gas. The product is a single Sampler that may be used in, but is not limited to shallow and deep water wells, production wells (e.g. shale or coalbed methane wells), monitoring wells and contaminated aquifers. More particularly, the present invention relates to investigating and monitoring microbial stimulation (e.g. increased methane production) downhole.

BACKGROUND SECTION

Global warming has been linked to greenhouse gas such as carbon dioxide that in excess trap heat resulting in warming of the atmosphere. The excess has been linked to burning of coal that provides other environmental impacts and human health effects due to release of other gases such as Sulphur dioxide, nitrogen oxides, mercury and other chemical products contributing to hazards such as acid rain and lung cancer.

Steps to mitigate these environmental hazards have been found by extracting natural gas such as methane that is released from coal beds. This release of methane has been found to result from coal degradation partly due to specific bacterial populations and enzymes. With the discovery that approximately 20% of natural gas is microbial in origin, identifying the specific microbial population that promotes degradation is critical, and has led to development of Microbial Enhanced Coal Bed Methane (MeCBM), which involves stimulating microorganisms to produce additional CBM from existing production wells.

Cost effective techniques to identify microbials have been found in DNA-sequencing. Not only has this technology been beneficial in isolating and identifying microbial communities for CBM studies, but has been applied in microbial ecology in deep waters evolutionary research.

Unfortunately, sampling subsurface microbial communities has been difficult due to studies relying solely on water and core samples to access or study the active subsurface microbial community. However, present Samplers that only acquire water do not adequately reflect the microbial densities and activities in the subsurface at selected locations. Microbials have been found to grow and attach to the subsurfaces found at the desired location and are less likely to be represented in sufficient numbers in mere water samples. Use of core samples are often prohibitively expensive to obtain, and difficult to collect in conditions similar to the desired environment. In instances, where the target area is a deep subsurface such as coal beds, the environment requires the core and water to be anaerobic, which is a costly process to achieve and to keep aseptic. Failure to duplicate the sample's environmental conditions including pressure, gas and temperature may change and destroy microbial attached to the core.

DESCRIPTION OF RELATED ART

Current use of Samplers and approaches to examine and investigate environments, such as the ocean, wells, reservoir conditions and indigenous, subsurface microbial communities have been restricted and limited.

Various Samplers are known in the art, but are not constructed and operative in a manner that prevents contamination of the sampled media or that allows for several samples to be collected at various depths within a hole or free body of water like the ocean or lake without requiring the Sampler to be in contact with an upper floor of a subsurface.

Figure 5:
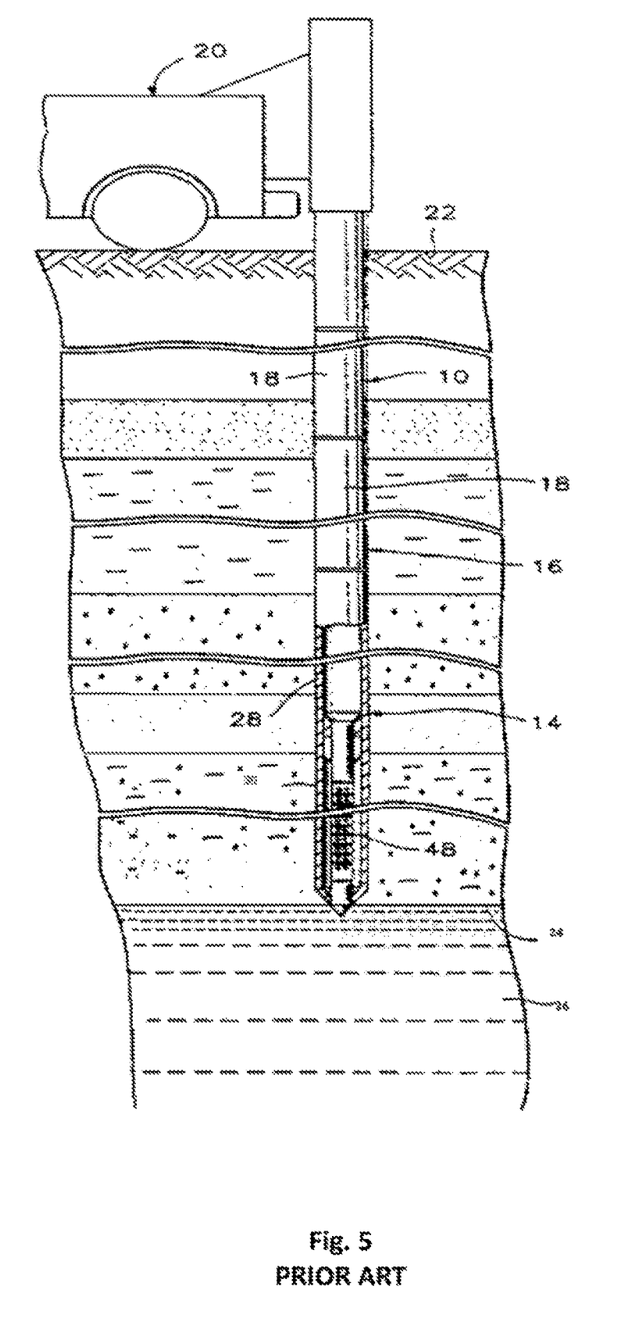
FIG. 5 illustrates a Sampler of the prior art.
Figure 6:
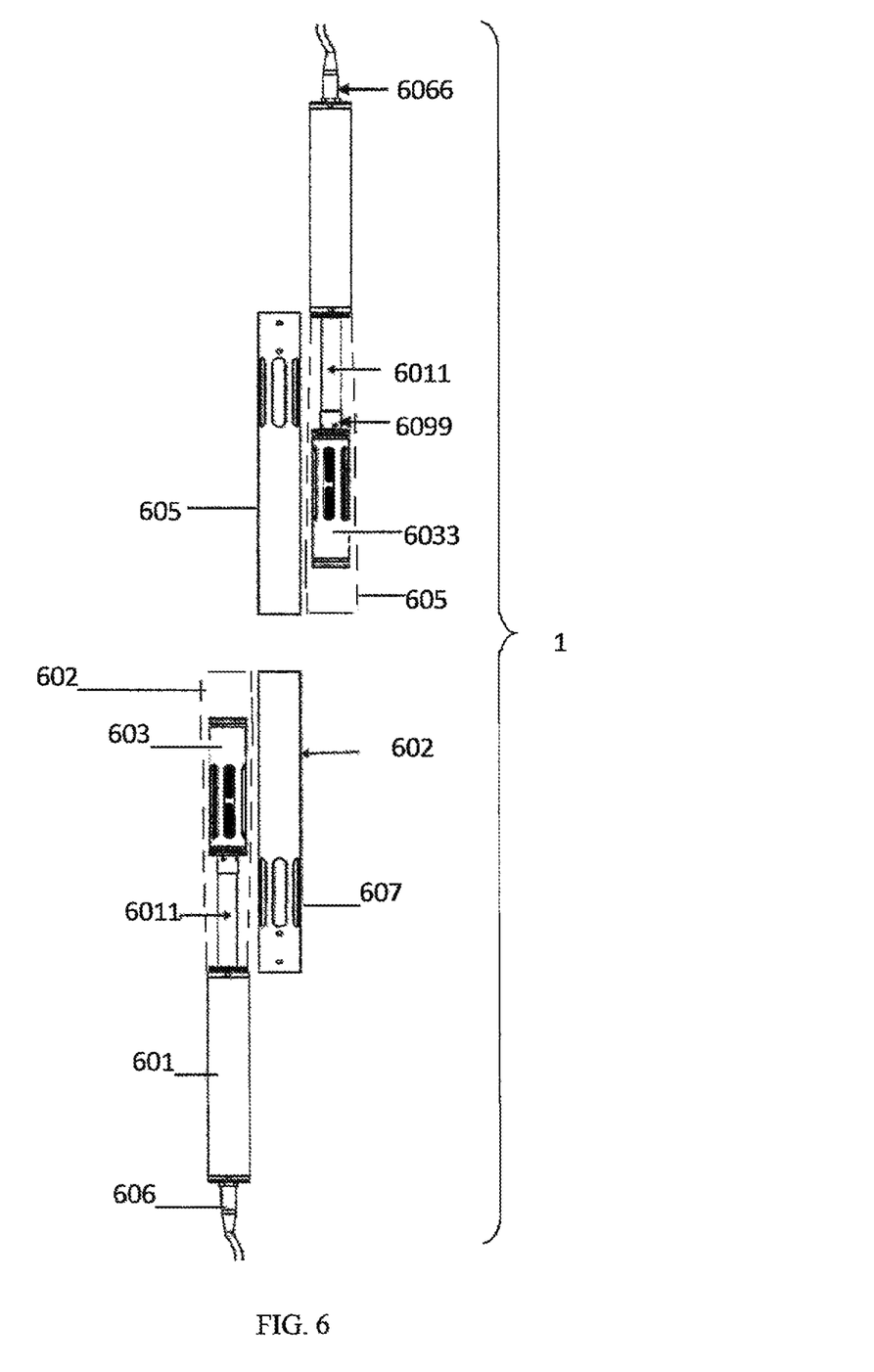
FIG. 6 depicts an alternate embodiment sampler with chambers 603, 6033 in a first and second housing 602, 605, with each chamber having a source 606, 6066 connected to an actuator 601, 6011. Each source through known methods independently sends signals to its connected actuator to extend or retract its piston 609, 6099 to push or pull a chamber 603, 6033 so that it is either aligned (placed) at slots 607, 6077 in either housing or moved from being aligned with the slots in a housing. Since each actuator is connected to an independent source, the actuators can be triggered to move at the same or different time.

An example of a sampler is shown in FIG. 5. U.S. Pat. No. 5,168,765. Sampler 10 has a lower unit 14 mounted on a tube string 18 that surrounds a screened sample tube 48. A push rod is inserted in the tube string for exerting a downward force to project the screened sample past the bottom cone member of 14 once Sampler reaches a target subsurface or upper extremity 24. Both water and gas may be pulled into the screened sample by static pressure in ground layer that screen screened sample tube projects in through the screened tube and rod from which it is pumped out. The depth of the Sampler is limited by length of tube and rod.

Alternatively, Samplers such as a diffusive microbial Sampler (DMS) may be capable of being closed mechanically due to weights located at its bottom pulling the Sampler closed. When the Sampler is lowered to a target having a ground floor, the weights at the bottom push up on the Sampler opening it, and allowing water or a targeted media to enter its chamber. After a period, the Sampler is then retrieved, the force of gravity of the weights pulls down on Sampler, and sliding chamber closed as it is being lifted. The mechanical closure results in a poor sealing that allows for contaminants to enter the sampling chamber when the component is lowered or retrieved from a specific target depth resulting from differing microbials and conditions found at various depths.

Likewise, in both Samplers, during testing of the collected media, in-situ conditions are not maintained. Changes in those conditions may result in release of or change of gas, pressure, acidity, change or loss of microbials. Such changes, and introduction of potential contaminants will result in unwanted constituents that may distort the results of the experiment and data collected.

The development of a single, multifunctional Subsurface Environment Sampler that may be used in shallow or deep depths in down-well or oceans that permit incubation of sediment, core and gas sealed containment has emerged as an alternative method to sample subsurface microbial communities that minimizes cost and contamination issues associated with traditional methods by maintaining in-situ testing conditions while allowing the sampler to serve as a reactor for on or off-site testing.

SUMMARY OF THE INVENTION

In order to solve the above mentioned problem, the present invention provides a Sampler completely controlled where its collection chamber is able to be sealed and opened, multiple times at various depths and times prior to being retrieved. Test such as identifications of gasses or microbial communities as well examining the effects of an introduction of a substance into a specific subsurface environment such as a nutrient may be performed on the Sampler either at a field site or a lab while maintaining in-situ conditions.

The Sampler disclosed by the present invention comprises a collection chamber with removable fittings inserted into ports within an end cap of the chamber. The size and shape of the Sampler may vary. Preferably the fluid volume that may be contained in the Sampler is 250 ml. The collection chamber contains a mechanical gasket such as an O-ring made of a compressible material elastomer or rubber protruding from its ends enabling sealing of the Sampler at depths greater than 250 feet. The chamber is placed within the mated housings including an actuator, having slots formed in one end of the housings to allow for a media to enter the chamber. Any known down-hole lowering mechanism preferably a cable reel or tool string may be a connected to the Sampler to lower or retrieve the Sampler at a desired depth. For use of wireline cables that provide transmits power and information, it can optionally be attached to a control box. Power and data may be transmitted wirelessly or through wires within the cable to the actuator or optional probes placed within the Sampler like PH, ORP or methane sensors as the source for in-situ testing. When power is transmitted to the actuator, the Sampler is signaled to either close by triggering the actuator's piston to extend pushing a connected chamber away from the slots, causing pressure exerted on the mechanical gasket to seal the chamber air tight within the housing or closed by retracting the piston causing the chamber to be pulled within slots. The ability to open and close may be triggered from control box on the ground attached to cable or through known wireless technologies such radio frequency (rf) by Integrated Circuit and board (PCB) within the Sampler connected to the actuator and portable power supply.

Another aspect of the present invention is that multiple collection chambers may be placed within the mated housings. Actuators that connect to the chambers may be placed either in one end of a housing within its perimeter, or each Actuator may be located at opposite ends of the mated housings. Slots may be located on both separate housings. Each Actuator may be connected to the same or different power and signal sources enabling each chamber to be either opened or closed at the same or different times.

The ability of a single Sampler to be opened and closed at multiple sites, to provide an air tight sealed chamber where contents within the chamber may be accessed at in-situ conditions provides for multiple advantages and uses.

The Sampler may be lowered in a dry or fluid environment, opened for a period of time (seconds, minutes, days, weeks, months) and closed to capture either fluids or gases. Probes within the Sampler may be used to transmit data of the contents without removal of the Sampler. Additionally, the Sampler may be retrieved and other probes may connected to the various fittings based on the desired test.

In areas where there is concern of contamination, such as studying tracking or methane production on its effects on water ways, aquifers or wells, the Sampler may be used to acquire water at specific depths maintaining in-situ conditions. The Sampler may be retrieved from its lowered depths, and the mated housing detached to allow for ease of handling. The closed housing may flipped such that the fittings connected to the collection chamber extend upward. A cap on the housing end covering ports and, optional interchangeable fittings may be removed. Fittings may be added to ports for connection to other apparatus to fill, pressurize, depressurize or degas the chamber. An apparatus for gas release such as a syringe may inserted into an air-lock fitting. Gas will rise filling the space within the syringe. The syringe may then pulled out and inserted into a gas analyzer such as a chromatograph.

Advantage of the Sampler, includes studying, the effects of incubating a certain media like coal, or glass beads and then injecting nutrient amendments in the chamber when sealed. Cores acquired at a specific depth may be placed in the screened collection chamber of the Sampler. The chamber due to the confined space allows for the core to maintain its integrity when placed in fluid like water, brines, and liquids to serve as a median for microbials to colonize and or form biofilm. The chamber is inserted back into a housing mating a first and second housings together. The Sampler may then be lowered to the specific depth and opened without contact with a subsurface floor. Over a specific time, the media will achieve the same condition as like material in the targeted area. Due to the Sampler's enclosure of its chamber and seal, it will maintain in-situ conditions while being retrieved. Optionally a thermal sleeve may be placed around the retrieved Sampler to allow it to incubate where temperature is a concern. The material that entered the collected chamber may then be studied for various test such as study coal degradation and microbial density either onsite, a lab or at a remote facility. Various substances or amendments such a nutrient may be inserted into the chamber to study its effects. The inserted substance may be lowered back to a specific subsurface location and opened to introduce the amendment to the targeted subsurface environment. After a predetermined sampling time, the Sampler may be then closed to study its effects on the media, such as for example coal bed methane enhancement. Optionally amendments may be inserted and examined within the Sampler, using the chamber solely as the reactor to study effects without placing Sampler back to the target area, since the Sampler through its ports allows of access and testing to be done in the Samplers Chamber set at in-situ conditions.

Once the Sampler has captured the selected subsurface environmental parameters of interest, the sampler is retrieved. It is contemplated that the Sampler may be used with or without the third housing in dry and fluid environments for various test evaluated at different times. The mated housings may be disassembled allowing for the sealed chamber, and its housing to be quickly replaced with another unit to eliminate delay of further testing. End caps on the sealed part of the Sampler may be removed allowing access to the chamber's, ports or fittings for various test. Since the chamber is sealed, the Sampler may be accessed onsite or transported offsite or to a remote facility for later retrieval or to serve as a reactor. By maintaining in-situ conditions, the Sampler is able to reduce factors that can impact sample, distort data, and reduce cost by eliminating the need to prepare in advance media that mirrors the selected environment of interest like anaerobic media.

BRIEF DESCRIPTION OF THE DRAWINGS

The subject matter and its advantages will become more apparent from the following detailed description and claims particularly when considered in light of the accompanying drawings:

DETAILED DESCRIPTION

Figure 1:
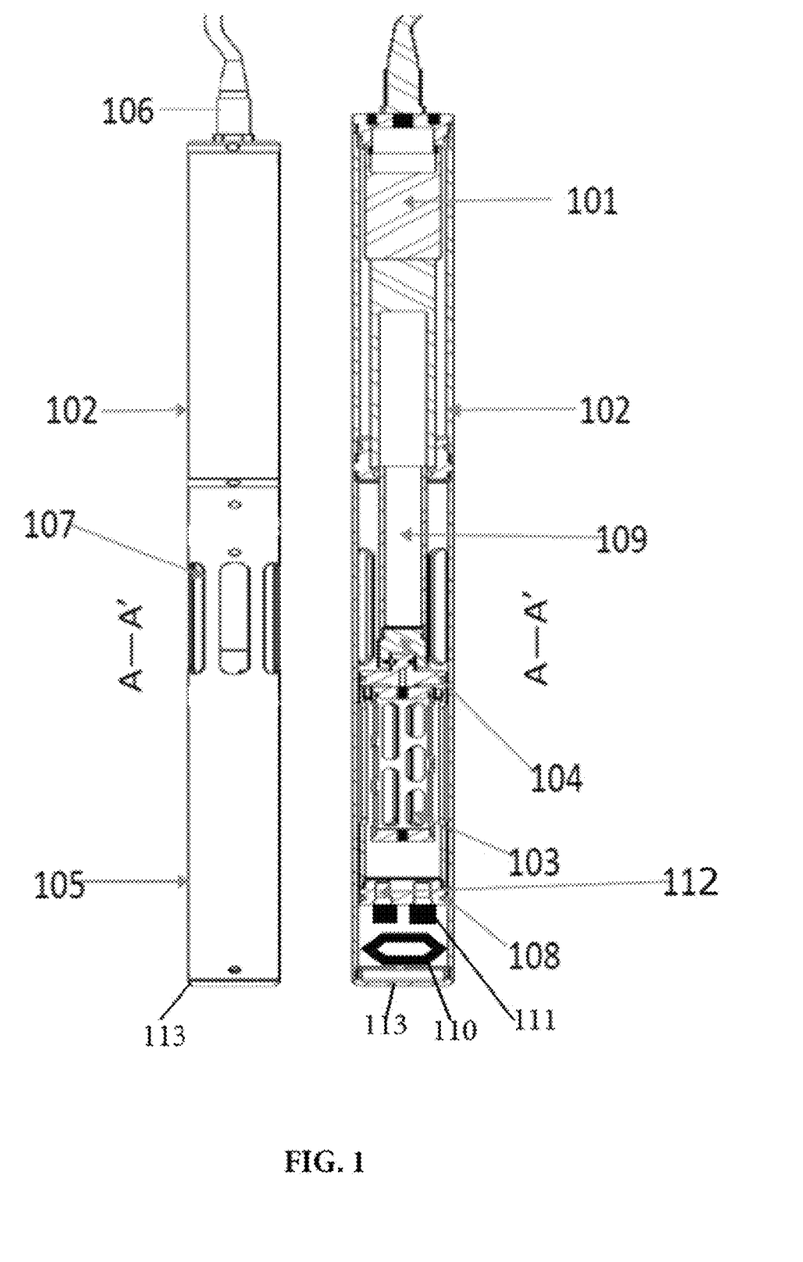
FIG. 1 is a schematic diagram of a preferred embodiment of a sampler assembled for collecting and evaluating subsurface environment for microbial, water and gas samples.

FIG. 1 depicts a preferred embodiment of a sampler suitable for inoculating, incubating and evaluating various materials in dry or fluid environments at shallow or deep depths. An actuator 101 is placed within a first housing 102 including metal and connected to a connection chamber 103 through a connector 104 such as male-female connectors, clamps, screws and the like. A second housing 105 including metal formed around the collection chamber is mated with the first housing. The second housing having a removable end cap 113 exposing fitting 111 placed inside ports 112 for extracting gas in chamber 103. Optional probes 110 may be placed adjacent removable cap 113 or alternatively in ports 112. A source 106 connected to actuator activates a piston 109 and pushes the chamber past slots 107 sealing the chamber within the second housing with a sealing material, such as compressible caps or rings 108. The metal being able to withstand pressure of at least 25 Torr to 5000 psi and at least temperatures −15 degrees Fahrenheit to 350 degrees Fahrenheit.

Figure 2:
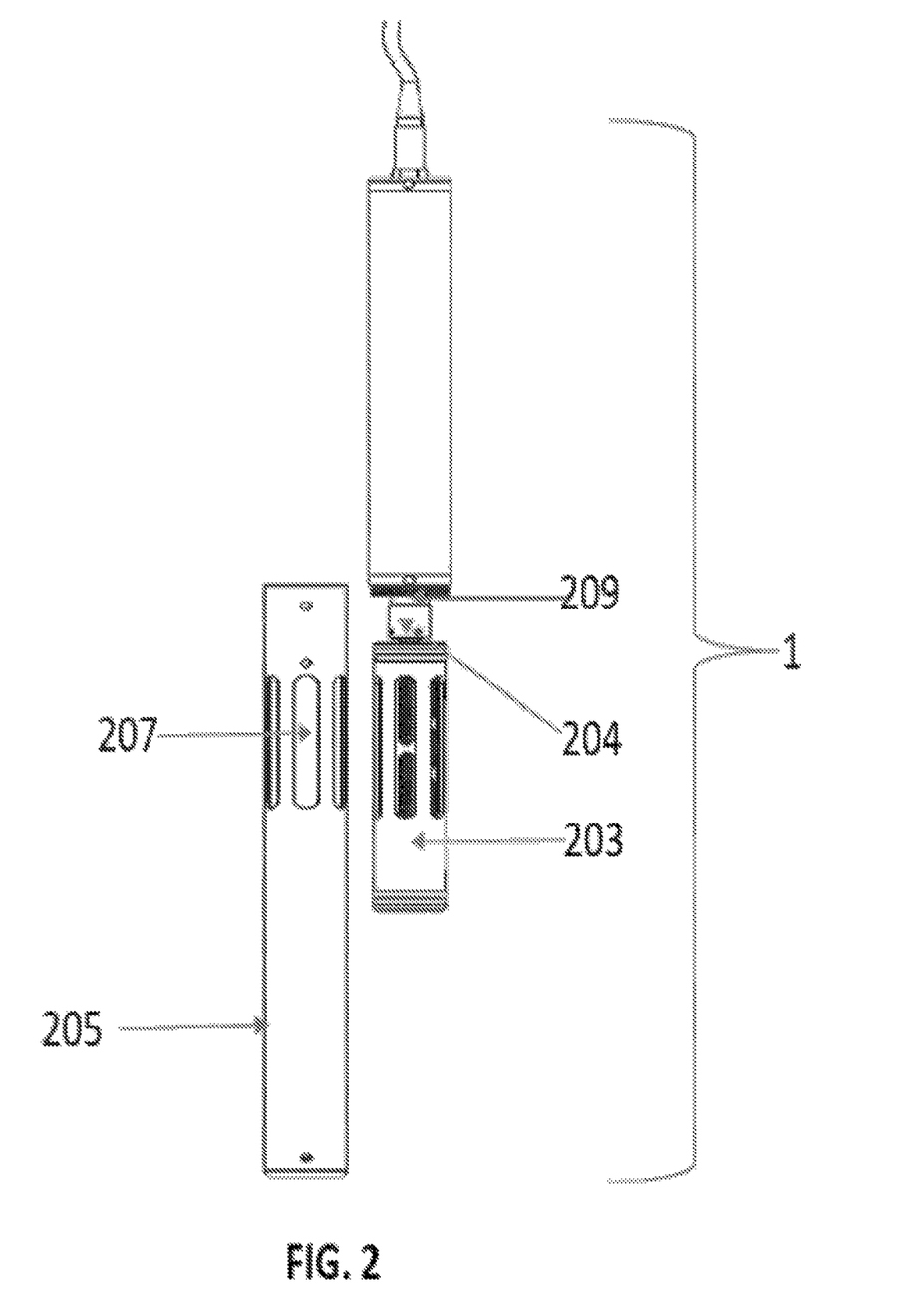
FIG. 2 depict a schematics diagram of actuator in closed position with piston retracted.

As shown in FIG. 2, the preferred embodiment shows an exploded view of the Sampler 1 preferably made from 316 stainless steel with piston 209 retracted with a connector 204 connected to a chamber 203 lined with slots 207 in the second housing.

Figure 3:
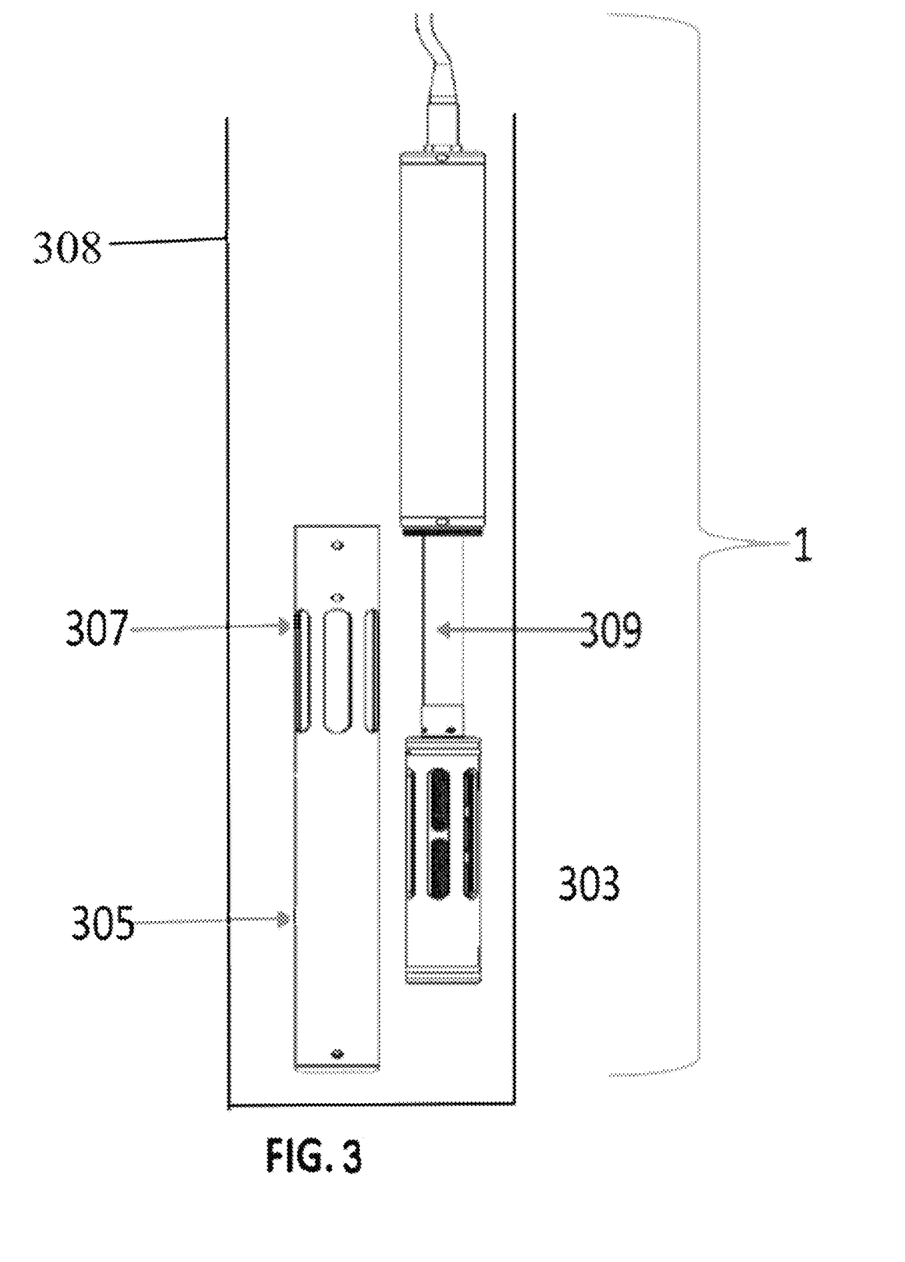
FIG. 3 depict a schematics diagram of actuator in open position with piston extended.

As shown in FIG. 3, the preferred embodiment shows an exploded view of the Sampler 1 with piston 309 extended with chamber 303 offset with slots 307 in the second housing 305. Optionally a thermal sleeve 308 may be placed around chamber.

Figure 4:
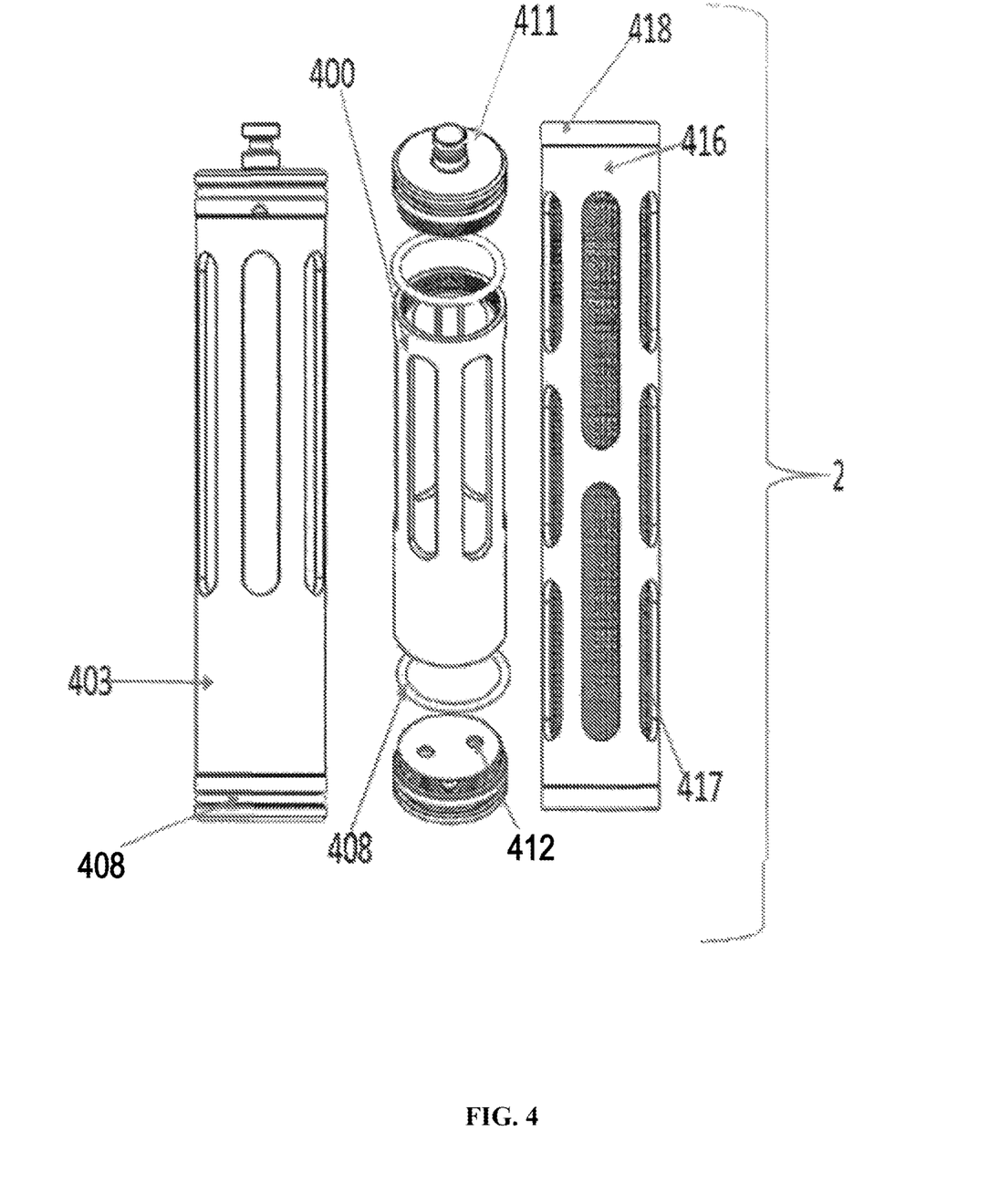
FIG. 4 is are exploded view of collection chamber including a housing and a screened microbial collection module.

FIG. 4 depicts an exploded view of a collection chamber 2, the collection chamber 403 includes a third housing 400 with end caps 411 having a sealing material 408 and ports 412 contained therein. A microbial collection 416 module includes end caps 418 and a removable screen 417 within placed in the third housing so that it can be replaced with various mesh sized to match the specific media being used. Likewise an optional filter may be added within the third housing to control microbe entry by size.

While, the invention has been described and shown in terms of what are considered to be the most practical and preferred embodiments, it is understood that the invention covers various modifications and similar arrangements included within the scope of the appended claims.

What is claimed is:

1. A Subsurface Environment Sampler comprising:
   a first housing including an actuator with a source connected to an end of the first housing to trigger the actuator;
   a second housing mated with the first housing with a removable cap placed on an end of the second housing;
   at least a collection chamber placed in the second housing;
   at least two slots formed in the second housing and surrounding an entire-outer perimeter of the second housing exposing the chamber to the environment;
   the actuator capable of closing the chamber from the environment by exerting force on the chamber to move the chamber completely pass by the slots, thereby creating a seal between the chamber and the second housing to maintain in-situ condition at depths greater than 250 feet.

2. A Subsurface Environment Sampler of claim 1, with the chamber comprising a third housing, and a screened microbial collection module placed in the third housing with caps formed on each end of the third housing.

3. A Subsurface Environment Sampler of claim 2, with each of the caps of the chamber including compressible material to seal the chamber.

4. A Subsurface Environment Sampler of claim 3, with each of the caps of the chamber including ports for removable fittings;
   wherein the Sampler is capable of being used to test gas, microbials and water.

5. A Subsurface Environment Sampler of claim 4, further including removable fittings allowing for connection of various apparatus, probes, test and data collection.

6. A Subsurface Environment Sampler of claim 3, wherein the screen is removable.

7. A Subsurface Environment Sampler of claim 3, further including data lines through a source connected for data transmission in real time without removing the Sampler from its sampling location.

8. A Subsurface Environment Sampler of claim 1, wherein the source is a cable connected to a control box.

9. A Subsurface Environment Sampler of claim 1, further includes a collection module inserted within the chamber.

10. A method of testing a subsurface environment by following steps in the order presented:
   (a) selecting a sampler having a first housing including:
      at least one actuator with a source connected to an end of the first housing to trigger the actuator,
      a second housing mated with the first housing with a removable cap placed on the end of the second housing,
      at least one chamber with ports for fitting placed in the second housing,
      at least two slots formed in at least the second housing surrounding an entire outer perimeter of the second housing exposing the chamber to the environment;
   (b) closing the chamber from the environment by sending signal to exert force on the chamber to allow the chamber to completely pass the slots and lowering the sampler to a specific depth;
   (c) opening the chamber by sending a signal to retract actuator that causes the chamber to align with the slots to expose the chamber to an environment at the specified depth;
   (d) closing the chamber using step (b) after a determined time to capture a fluid or gas;
   (e) retrieving Sampler from the depth while maintaining in-situ conditions.

11. A method of testing a subsurface environment of claim 10, wherein the chamber includes a removable screen.

12. A method of testing a subsurface environment of claim 10, further including lowering the Sampler; wherein closing the Sampler maintains an air tight seal at depths greater than 250 feet, and at least performing steps (C)-(d) on two different occasions prior the retrieving step.

13. A method of testing a subsurface environment of claim 10, further including between the steps of (d) and (e) collecting data with probes included with the Sampler.

14. A method of testing a subsurface environment of claim 10 further including after step (e) placing the chamber in a thermal sleeve.

15. A method of testing a subsurface environment of claim 10, further comprising a step of using a second chamber in the first or second housing which is controlled to be opened and closed at the same and at different times than the first chamber.

16. A method of testing a subsurface environment of claim 10, further comprising after step (e) detaching the second housing and sealed chamber from the first housing and replacing with another chamber and housing.

17. A method of testing a subsurface environment of claim 10, further comprising removing cap from the second housing, tilting the sampler, inserting a tool into fittings placed in the ports to extract gas.

18. A Subsurface Environment Sampler comprising:
a first housing mated with a second housing;
a first collection chamber placed in the first housing;
a second collection chamber placed in the second housing;
slots formed in the first and the second housing, and surrounding an entire outer perimeter of the first and second housing to expose a chamber aligned with the slots to an environment;
a first actuator in the first housing capable of exerting a force on the first chamber,
wherein the first chamber is aligned with slots in the first housing or made offset from the slots in the first housing to seal the first chamber in the first housing;
a second actuator in the second housing capable of exerting a force on the second chamber,
wherein the second chamber is aligned with slots in the second housing or offset from the slots in the second housing to seal the first chamber in the second housing.

19. A Subsurface Environment Sampler of claim 18 further comprising:
a source connected to the first actuator;
a second source connected to the second actuator;
wherein each actuator is connected to an independent source, such that the actuators are capable of being activated to move at the same or different time and direction.

20. A Subsurface Environment Sampler of claim 19, including a housing cap on a top and bottom portion of the first and second chamber;
each of the caps including compressible material;
whereby the first and second chamber are capable of being sealed with a non-slotted portion of the first or second housing,
by the compressible material of each of caps being compressed between the chamber caps and the first and second housing.

* * * * *